United States Patent [19]
Reynolds

[11] Patent Number: 6,149,623
[45] Date of Patent: Nov. 21, 2000

[54] DELIVERY SYSTEM FOR PHARMACEUTICALS PACKED IN PHARMACEUTICAL VIALS

[75] Inventor: David L. Reynolds, LacBrome, Canada

[73] Assignee: Duoject Medical Systems Inc., Bromont, Canada

[21] Appl. No.: 09/114,063

[22] Filed: Jul. 13, 1998

Related U.S. Application Data

[63] Continuation-in-part of application No. PCT/CA97/00017, Jan. 10, 1997, which is a continuation-in-part of application No. 08/584,049, Jan. 11, 1996, abandoned.

[51] Int. Cl.[7] .................................................. A61M 37/00
[52] U.S. Cl. ......................... 604/82; 604/201; 604/187
[58] Field of Search ........................... 604/232, 82, 187, 604/191, 192, 201

[56] References Cited

U.S. PATENT DOCUMENTS

| | | |
|---|---|---|
| 3,563,373 | 2/1971 | Paulson . |
| 3,872,867 | 3/1975 | Killinger . |
| 4,060,082 | 11/1977 | Lindberg et al. . |
| 4,516,967 | 5/1985 | Kopfer . |
| 4,568,346 | 2/1986 | van Dijk . |
| 4,583,971 | 4/1986 | Bocquet et al. . |
| 4,675,020 | 6/1987 | McPhee . |
| 4,886,495 | 12/1989 | Reynolds .......................... 604/191 |
| 5,171,214 | 12/1992 | Kolber et al. . |
| 5,364,369 | 11/1994 | Reynolds . |
| 5,472,022 | 12/1995 | Michel et al. .......................... 141/1 |
| 5,554,125 | 9/1996 | Reynolds .......................... 604/187 |
| 5,827,262 | 10/1998 | Neftel et al. . |

FOREIGN PATENT DOCUMENTS

| | | |
|---|---|---|
| 0335378A | 10/1989 | European Pat. Off. . |
| WO 90/03536A | 4/1990 | WIPO . |
| WO 92/11987A | 7/1992 | WIPO . |
| WO 96/14820 | 5/1996 | WIPO . |
| WO 97/20536 | 12/1997 | WIPO . |

*Primary Examiner*—Glenn K. Dawson
*Assistant Examiner*—Jeremy Thissell
*Attorney, Agent, or Firm*—Ridout & Maybee

[57] ABSTRACT

A system is provided for providing syringes filled with pharmaceuticals whose components must be stored separately, using an active ingredient in a pharmaceutical vial, a diluent in a protosyringe such as a bottomless vial or a cartridge, and a combiner assembly which enables the content of the pharmaceutical vial to be transferred into the protosyringe and converts it into a ready-to-use syringe on activation. The combined assembly included a tubular body having recesses at opposite ends for receiving capped ends of the vial and the protosyringe, and a hub and needle assembly between penetrable sheaths or shields which acts on activation of the assembly to enable the transfer and conversion referred to above. Components of the system may also be used to convert protosyringes and pharmaceutical vials containing pharmaceuticals into delivery systems.

23 Claims, 9 Drawing Sheets

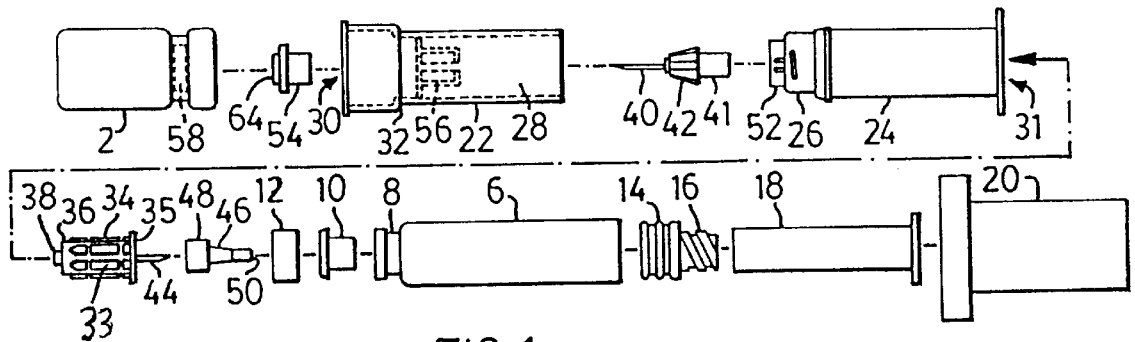
FIG.1
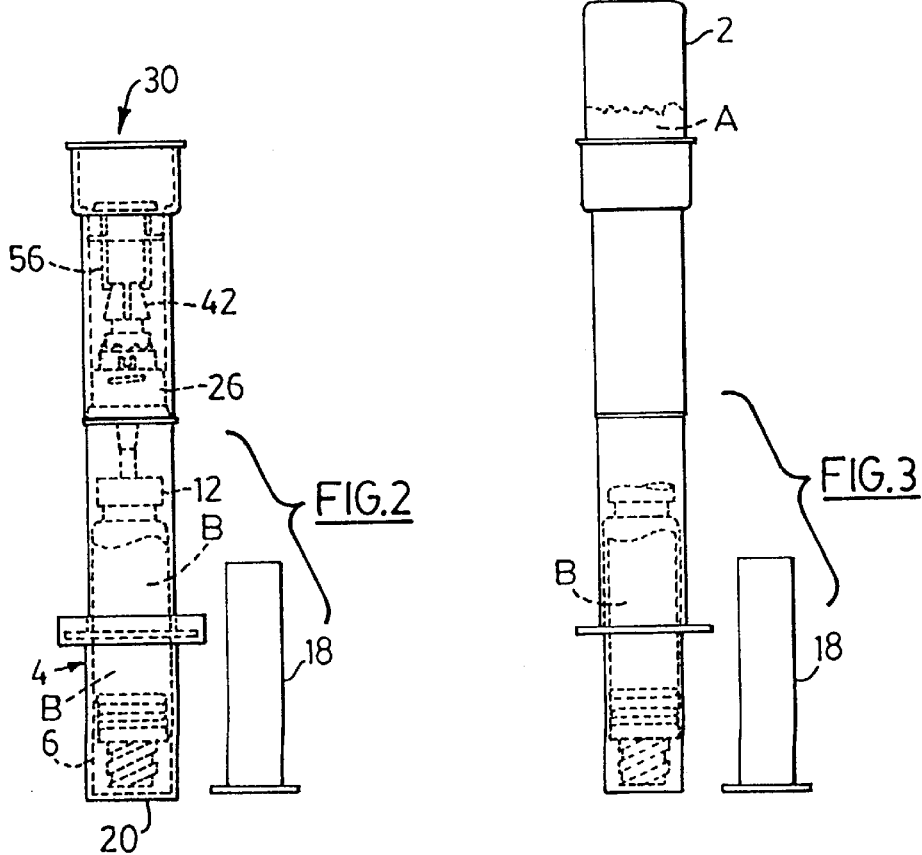
FIG.2
FIG.3

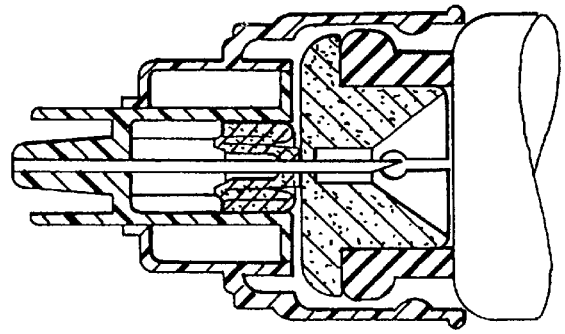
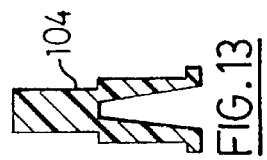
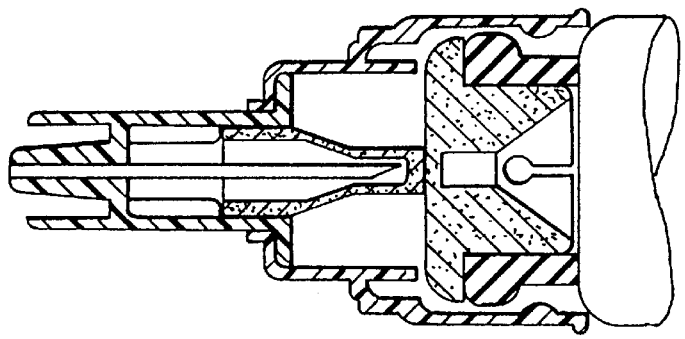
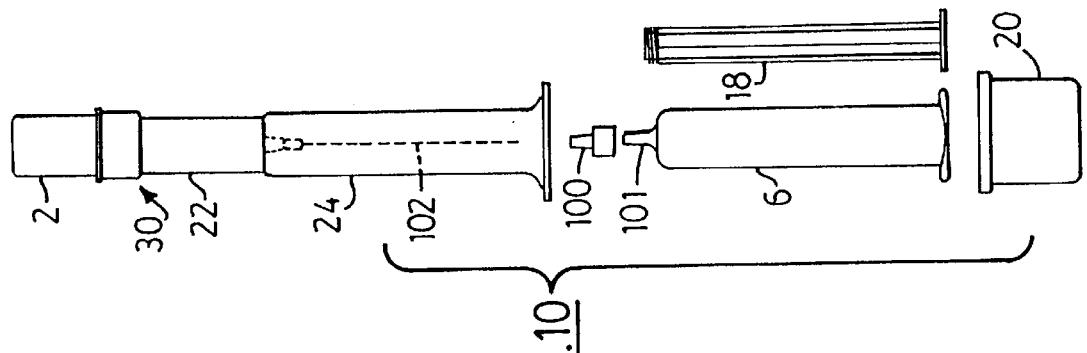
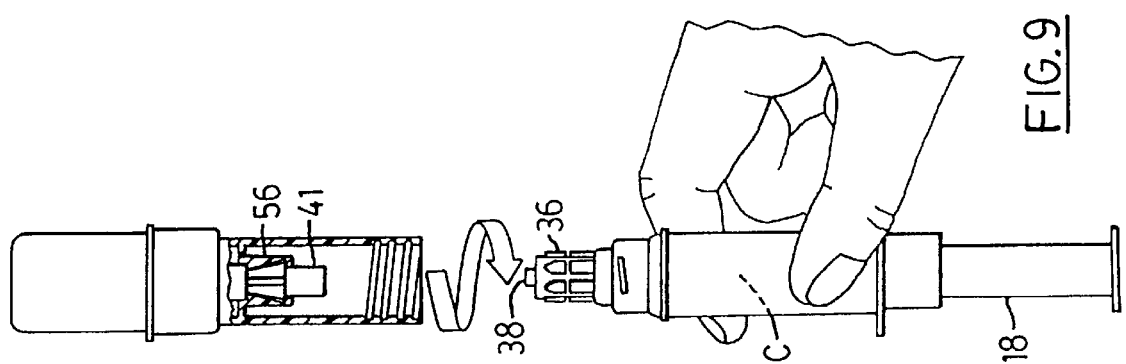

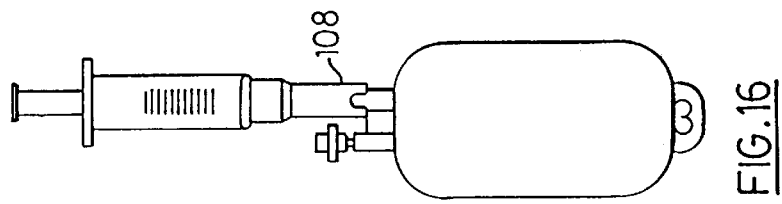
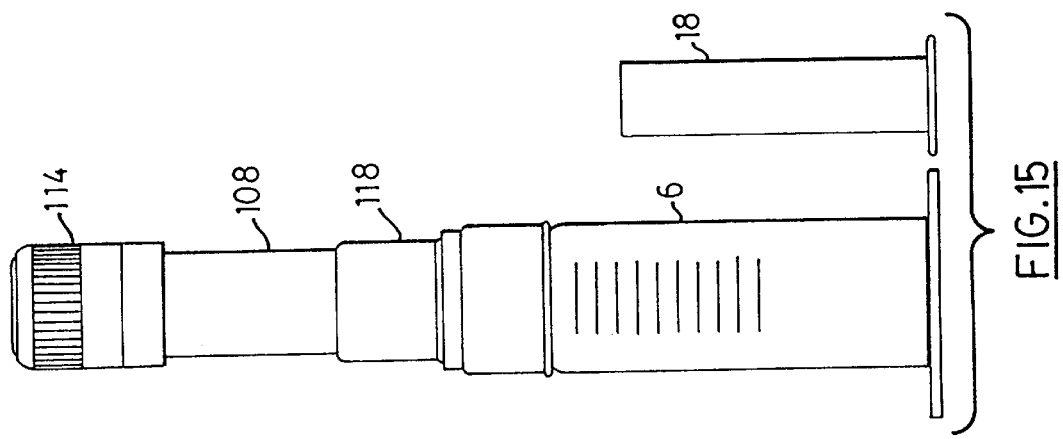
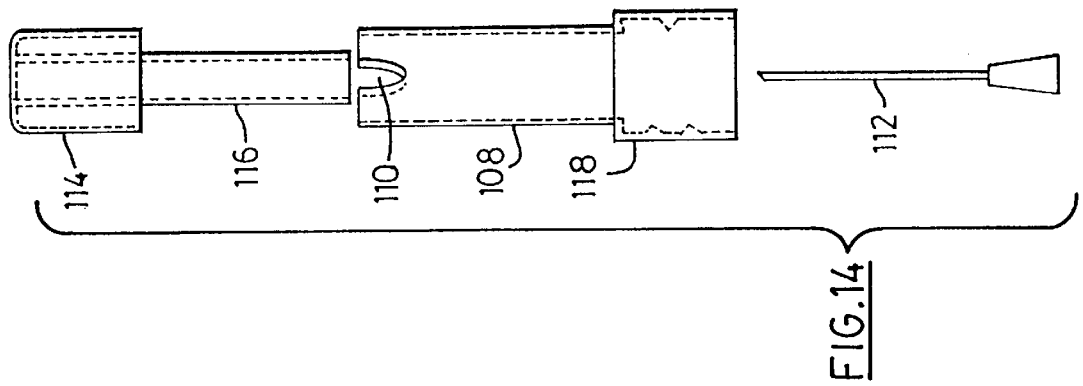

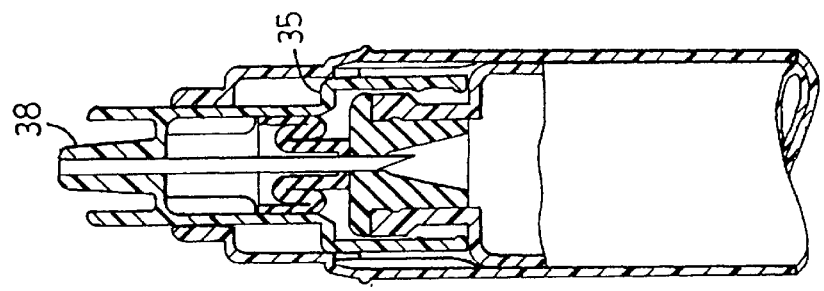
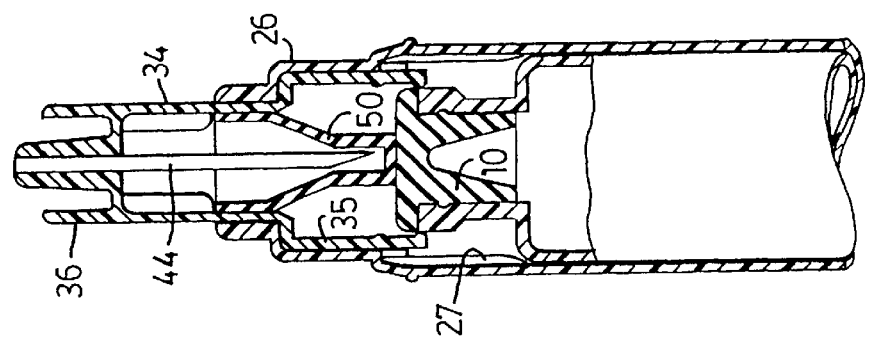
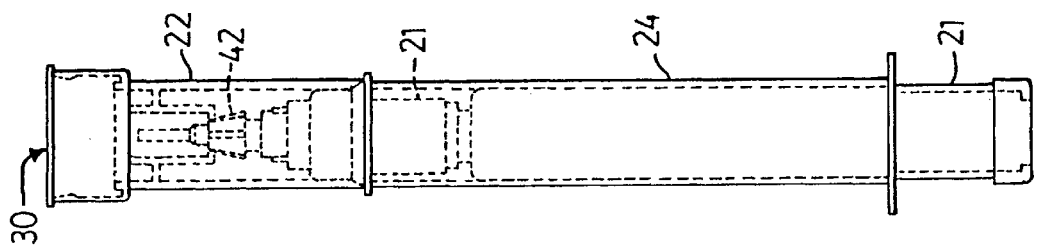
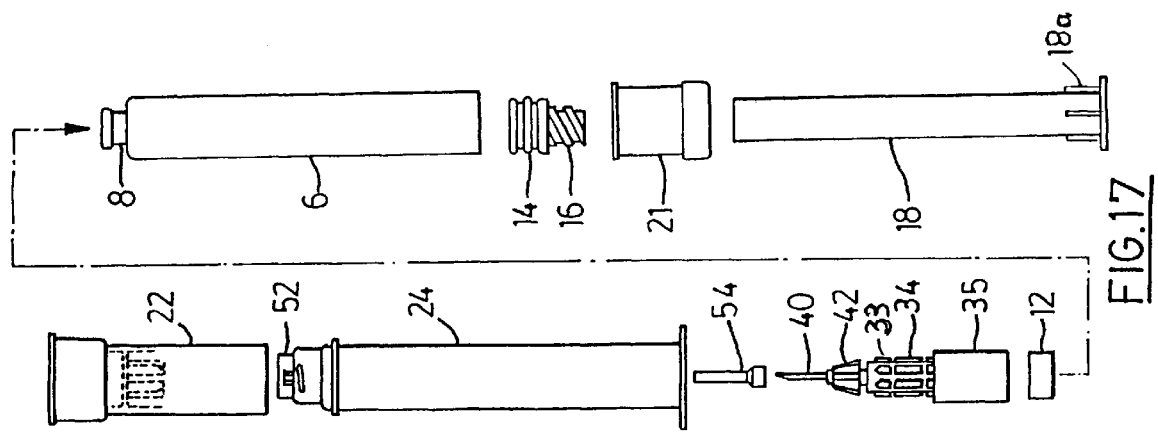

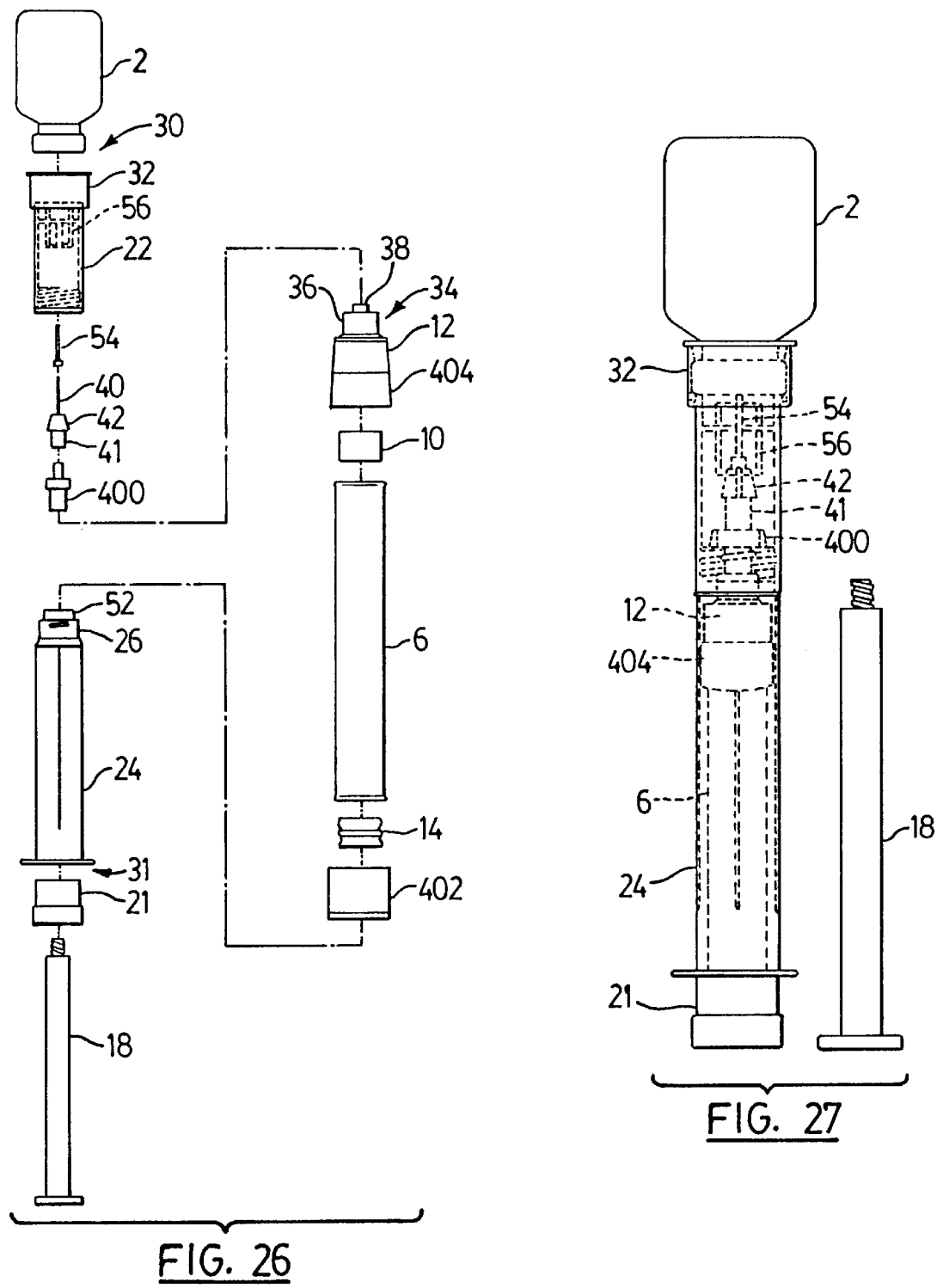

DELIVERY SYSTEM FOR PHARMACEUTICALS PACKED IN PHARMACEUTICAL VIALS

This application is a continuation-in-part of International Patent Application PCT/CA97/00017 filed Jan. 10, 1997, which is a continuation-in-part of application Ser. No. 08/584,049 filed Jan. 11, 1996 and now abandoned.

This invention relates to delivery systems for multiple component pharmaceutical preparations.

Many pharmaceutical preparations must be distributed as two or more separate components which can only be combined shortly before administration of the preparation, usually because the combined preparation is subject to rapid deterioration or otherwise unstable, and the components are only stable when stored separately. Typically at least one component of such a preparation is a liquid which acts as a solvent, diluent or carrier for the other component.

Traditionally such preparations have been prepared shortly before administration by taking one component packaged in a conventional pharmaceutical vial having a neck closed by a penetrable elastomeric stopper secured to a neck of the vial by a cap, taking a second liquid component in a hypodermic syringe, injecting the second component into the vial through the stopper, swilling the vial impaled on the syringe to dissolve, dilute or suspend the first component in the second component, and aspirating the combined components back into the syringe by withdrawing its plunger. This procedure requires a degree of dexterity, is subject to the errors commonly associated with manual on-site preparation of pharmaceuticals, and may compromise sterility. If a third component is used, the procedure must be repeated.

In endeavours to overcome these problems, many proposals have been made for systems to provide prepackaged two component pharmaceuticals, but these tend to suffer from one or more problems of their own such as complex and expensive structure requirements for specialized filling equipment, complex manipulation at the time of use, and often most serious of all, a heavy burden in time and expense in obtaining regulatory approval for a new product.

U.S. Pat. No. 3,872,867 (Killinger) utilizes a tubular assembly incorporating a double ended cannula, into which two pharmaceutical vials are pressed in order to combine components in the two vials. The system requires that one of the vials is under vacuum at pressure, and merely results in a vial containing the combined product, which must still be transferred to a syringe for administration.

U.S. Pat. No. 3,563,373 (Paulson) discloses an arrangement utilizing two cartridges in tandem for packaging a two component pharmaceutical, utilizing an intermediate assembly incorporating a double ended needle, which penetrates the piston of one cartridge and neck stopper of the other. The arrangement cannot utilize a standard pharmaceutical vial.

U.S. Pat. No. 4,060,082 (Lindberg) also requires two syringes in tandem for combining a two component pharmaceutical, as well as specialized auxiliary pistons in the syringes.

U.S. Pat. No. 4,583,971 (Bocquet et al) discloses apparatus for transferring liquid through a cannula from a flexible container to dissolve a pharmaceutical, and returning the solution to the flexible container. The system is dependent upon manipulation of a tangible closure through the flexible container and could not be used to transfer liquid from a syringe to a pharmaceutical vial and back again.

U.S. Pat. No. 5,171,214 (Kolber et al) discloses a combination of a vial assembly, a syringe assembly, and an adapter for attaching the vial assembly to the syringe assembly so that a liquid constituent may be transferred from the syringe to the vial and the admixed compounds returned to the syringe. A special vial and special syringe are required, and indeed the system is predicated upon the use of a proprietary vial assembly.

An object of the present invention is to provide a delivery system for two component pharmaceuticals which is economical to manufacture, easy to manipulate, and can minimize regulatory burdens.

SUMMARY OF THE INVENTION

According to the invention, there is provided an activation assembly for preparing a prefilled syringe from separately prepackaged components of a multicomponent pharmaceutical preparation, the assembly comprising a two part tubular body; the body defining in a first part a first cylindrical recess at one end of a diameter to receive, as a sliding fit, a discharge end of cylindrical body of a protosyringe at which end is located a closure, broachable on activation of the protosyringe, the recess also receiving a substantial portion of the cylindrical body of the protosyringe, which contains a first, liquid component of the pharmaceutical preparation and which is provided at its opposite end with a piston displaceable longitudinally of the cylindrical body and forming a hermetic seal therewith; a second cylindrical recess defined in the other end of the tubular body by a second detachable part to receive a cap securing a penetrable closure at the neck of the pharmaceutical vial containing a second component of the pharmaceutical preparation; the tubular body defining in said first part a passage connecting the cylindrical recesses; a hub movable longitudinally of the tubular body within the passage; a cannula extending longitudinally of the tubular body from said hub to a distal end directed towards the second recess; a penetrable shield member covering the distal end of the cannula and located to contact a penetrable closure of a pharmaceutical vial inserted in the cylindrical recess, and a hollow cylindrical overcap concentric with the hub assembly and located within the tubular body in the first cylindrical recess, the overcap being connected to the hub to limit movement of the latter into the passage; the depth of the cylindrical recesses, the length of the passage connecting the recesses, the extent of the cannula from the hub, and the location of the overcap i the first cylindrical recess being such that upon a protosyringe received in the first cylindrical recess and a vial received in the second recess being displaced towards each other, the overcap is displaced onto the discharge end of the protosyringe and the hub moves longitudinally so that the cannula penetrates the penetrable shield member and the penetrable closure of the vial to place the cap of the protosyringe and the vial in fluid communication through the cannula;

wherein the protosyringe and the vial can be driven directly towards each other to effect penetration of the shield member and the penetrable closure of the vial, wherein a portion of the hub supporting the cannula is separately formed and detachable from the hub assembly, the hub assembly having a luer on which said separately formed portion is releasably lodged, and wherein means is provided within the detachable part of the tubular assembly to detain, within the tubular assembly, said one end of the cannula when the cannula is driven into a position into a position penetrating the cap of the pharmaceutical vial.

Two terms used in the preceding paragraph and elsewhere in this specification and the appended claims require mention. A 'protosyringe' is an assembly intended to form the basis of a prefilled syringe but requiring the addition of components to form a complete syringe. At minimum, it includes a cylindrical body containing at least a component of a pharmaceutical product, the body being closed at one end by a broachable closure and being at an opposite end with a piston connected to or provided with means for connection to an activating plunger so that the latter may be used to displace the contents of the body. Protosyringes include bottomless vials as described in my U.S. Pat. No. 5,364,369; cartridges; and prefilled syringes requiring at least addition of an overcap as defined below and introduction of a further component of the pharmaceutical product to provide a ready to use syringe. An 'overcap' is a cap adapted to be lodged on the cap of a protosyringe and providing means for supporting a needle or other instrumentality through which contents of a syringe formed from the protosyringe may be discharged. In some instances, a complete prefilled syringe itself may be used as a protosyringe if it has a luer connection closed by a cap of penetrable material over which an overcap may be received.

The invention also extends to the combination of such an assembly with a protosyringe and/or pharmaceutical vials already engaged in their associated cylindrical recesses. If the protosyringe is already engaged in the first cylindrical recess, its free end may be covered by a removable cap to prevent accidental projection into the cylindrical bottom resulting in premature actuation of the assembly. When a protosyringe or vial is preengaged in its cylindrical recess, the associated sealing member in the assembly is in resilient contact with the penetrable closure of the vial in areas concentric with the cannula so as to help maintain sterility of areas of the sealing members and closures intended to be penetrated by the cannula.

The hub assembly and a modified overcap may also be utilized in conjunction with a protosyringe or pharmaceutical vial to provide alternative delivery systems for pharmaceuticals contained in the protosyringe or vial.

Further features of the invention will be apparent from the following description of embodiments of the invention.

IN THE DRAWINGS

FIG. 1 is an exploded view of the components of an assembly according to the invention, including both a protosyringe, in this case a bottomless vial, and a pharmaceutical vial;

FIG. 2 illustrates an assembly according to the invention, including a bottomless vial, as it might be shipped;

FIG. 3 illustrates a similar assembly, but further including a pharmaceutical vial, ready for activation;

FIG. 9 shows upper portions of the assembly being removed, leaving a syringe ready for application of a needle or other discharge means;

FIG. 10 shows a partially exploded view of a modified embodiment of delivery system utilizing a different form of protosyringe;

FIGS. 11 and 12 are fragmentary sectional views of an alternative form of syringe socket and associated parts which permit elements of the delivery system to be used in further embodiments of delivery system in conjunction with prefilled protosyringes or pharmaceutical vials;

FIG. 13 shows in section a cap which may be applied to a luer on a hub portion of the embodiment of FIGS. 11 and 12 to enable the hub to be driven from the position to FIG. 11 to that of FIG. 12 to activate a prefilled protosyringe;

FIG. 14 shows in an exploded view parts of an alternative activation system for use with the embodiment of FIGS. 11 and 12 so as to activate a syringe or vial for use in conjunction with a standard flexible mini-bag;

FIG. 15 shows an assembled syringe ready for activation;

FIG. 16 shows an activated syringe applied to a mini-bag;

FIG. 17 is an exploded view illustrating components of a presently preferred modification of the embodiment of FIGS. 1–9;

FIG. 18 shows the parts shown in FIG. 17 assembled ready for use, less the plunger;

FIGS. 19 and 20 illustrate a presently preferred modification of the embodiment of FIGS. 11 and 12;

FIGS. 26 and 27 are exploded and assembled views of a further embodiment of the invention.

DESCRIPTION OF THE PREFERRED EMBODIMENTS

Figure 8:
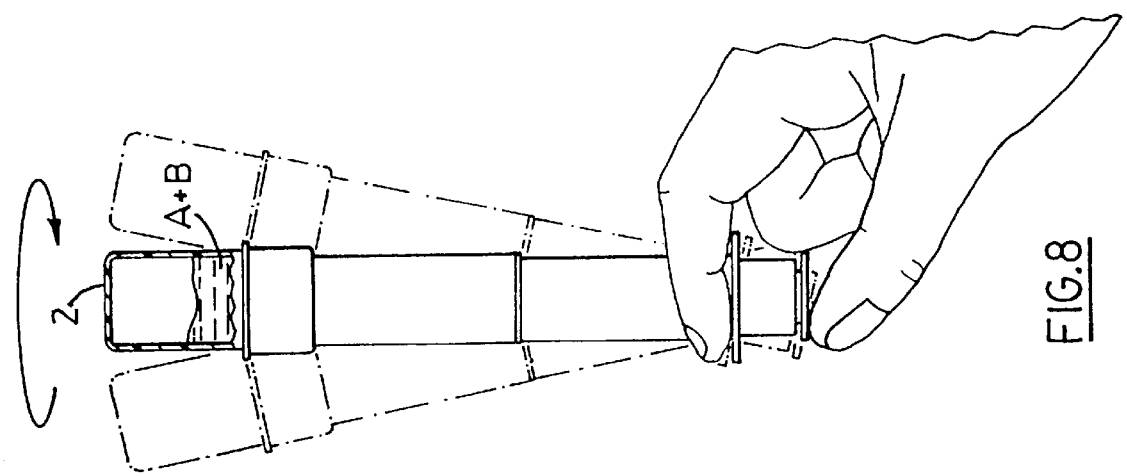
FIG. 8 is a view showing a mixing step.

Referring first to FIGS. 1 to 3, the parts are shown of an assembly for preparing a syringe containing a pharmaceutical preparation, components A and B of which are contained respectively in a pharmaceutical vial 2 and a protosyringe in the form of a bottomless vial 4 consisting of a cylindrical body 6, open at one end and provided with a neck 8 at its other end, the neck being closed by an elastomeric closure 10 secured in place by a metal cap 12 crimped over the neck. A piston 14 is lodged in the open end of the body, the piston being provided with means 16 by which a detachable plunger 18 may be secured to the piston. The plunger will normally be shipped detached from the piston, both to reduce the overall length of the assembly, and to permit a removable cap 20 to be applied over a projecting end of the bottomless vial 4 as shown in FIG. 2 so as to prevent inadvertent premature activation of the assembly.

At least one of the components A and B is liquid; usually it will be convenient to locate a liquid component in the bottomless vial but it would be possible to locate a solid component in the bottomless vial provided that the latter also contains an air or gas volume sufficient to displace liquid contents of the vial 2.

Since a typical two component pharmaceutical for administration via a syringe comprises an active ingredient and a liquid solvent, diluent or carrier (hereinafter collectively referred to as diluent for convenience) which in the majority of cases will be one of only a few different types (most usually distilled water), it will usually be advantageous to place the active component in the vial 2; this is because in many, if not most cases, a suitable vial package of the active ingredient will already be certified by regulatory cylindrical recess 31 into which may be slid the body 6 of the bottomless vial 4, although not initially to the full extent permitted by the depth of the recess.

The end portion 26 of the syringe socket includes a guide 52 with detents 53 for controlling longitudinal movement of a hub 34 having gapped longitudinal ribs 33. The hub is formed at a front end with a liquid delivery conduit through a standard luer as utilized in the industry for coupling needles, or other delivery instrumentalities forming liquid delivery conduit extensions, to syringes and other sources of liquid pharmaceuticals. Such a luer comprises an internally threaded socket 36 for locking a needle in place, and a tapered central spigot 38 for establishing a seal with a complementary socket on the needle. In the present instance, a hollow transfer needle 40 has a socket 41 lodged on the central spigot, but is not provided with threads to engage those of the socket 36, so the needle 40 may be pulled from the spigot 38. A tapered shoulder 42 is formed on the transfer needle 40. The hub 34 has a hollow needle or cannula 44 projecting from its end opposite the spigot 38 and in communication with a central passage in the spigot. A flexible needle sheath or shield 46 of thin rubber covers the needle 44, having a portion 48 engaging a socket in the end of the hub 34, and a flattened end 50 over the free end of the needle. Internally of the guide 52, the end portion 26 of the syringe socket also contains an extension of the cylindrical recess 31 dimensioned to provide an overcap which is a press fit over the cap 12 of the bottomless vial 4.

The vial coupling 22 has a passage extending from recess 30 which receives vial 2 to its internally threaded end, the passage being closed by a rubber stopper or shield 54. Between the rubber stopper and the internally threaded end of coupling 22, passage is formed internally with resilient pawls 56 which will detain the shoulder 42 of the needle 40 when the latter is pressed past the pawls.

The assembly just described may be shipped on its own with neither vial installed, in which case a removable cover (not shown) will be required to cover the cylindrical recess in the coupling 22 to maintain sterility, or with one or both vials installed (see FIGS. 2 and 3). When a vial 2 is installed, any removable central portion of a cap 60 covering a penetrable closure 58 of the vial is flipped off, so that the penetrable closure may contact a rib 64 on the stopper 54 to enclose an axial sterile zone of the two rubber parts 58 and 54. Likewise, an axial zone of the closure 10, similarly exposed, contacts the end 50 of the needle sheath 46 to provide protected zones on the contacting rubber parts.

Figure 6:
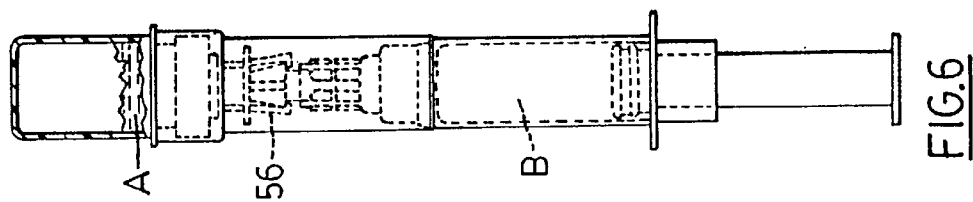
FIG. 6 is a view of the assembly corresponding to FIG. 3, after activation.
Figure 5:
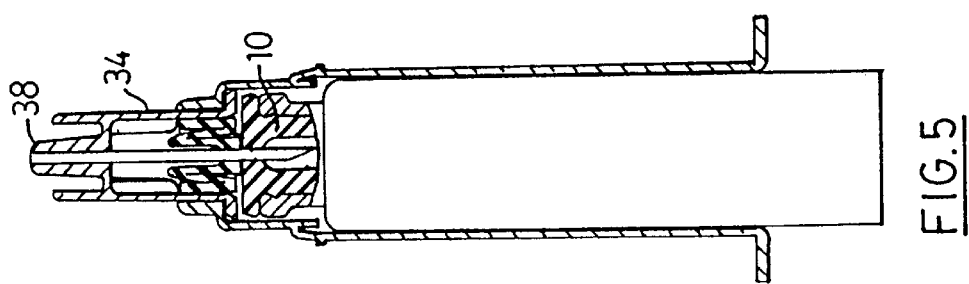
FIG. 5 is a similar view to FIG. 4, but showing the illustrated components in the relationship which they assume after activation of the assembly in order to prepare a completed prefilled syringe.
Figure 4:
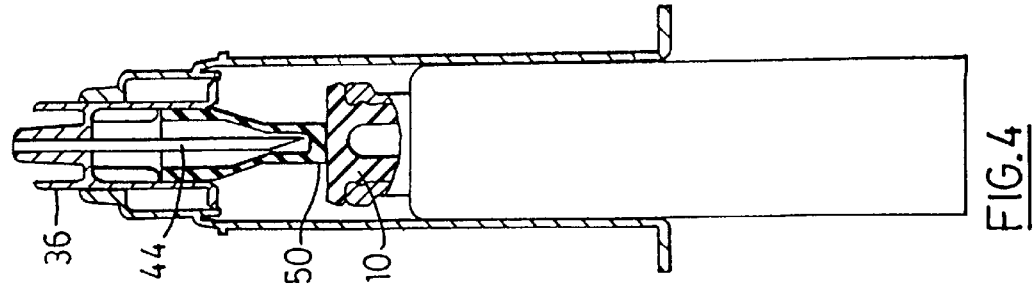
FIG. 4 illustrates in part sectional view components of an assembly according to FIG. 3, but with upper components removed for clarity.

In order to activate the assembly, after installation of the vials to provide the arrangement shown in FIG. 3, the bottomless vial is pressed into the syringe socket 24, and the plunger 18 is attached to reach the condition shown in FIG. 6.

Thereafter, the assembly is inverted and plunger 18 is activated to project the liquid content B from the bottomless vial into the pharmaceutical vial, (see FIG. 7), the assembly then being swilled as shown in FIG. 8 to dissolve, mix or suspend the contents of the vial 2 in the liquid, which is then aspirated back into the bottomless vial by withdrawing the plunger to reach a condition similar to that of FIG. 6, except that component A is now incorporated into component B to leave a product C in the bottomless vial. The vial 22 is now unscrewed from the syringe socket 24 and withdrawn, taking with it the transfer needle 40 which is pulled off the spigot 38 by the pawls 56, thus leaving the luer of hub 34 ready to receive a needle or other fluid connection instrumentality, and providing a completed ready to use syringe, filled with the two component pharmaceutical (see FIG. 9). The hub 34 is retained on the cap 12 of the bottomless vial by the syringe socket 24, with the needle providing a passage between the body 6 and the luer 36, 38.

Figure 7:
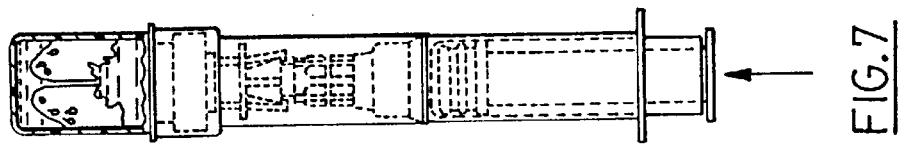
FIG. 7 is a view of the assembly after the plunger has been pressed upwardly to transfer liquid from the bottomless vial to the pharmaceutical vial.

If the initial position of liquid and solid components is reversed, the step of FIG. 7 may be performed without inversion, with reciprocation of the syringe plunger being used to force air or gas from the vial 4 to the vial 2, and liquid from the vial 2 to the vial 4.

A presently preferred modification of the assembly described above is shown in FIGS. 17 and 18, in which the same reference numerals are used to designate similar parts, and only the differences are described. In this modification, the flange 35 of the hub 34 is extended to form the overcap, and the portion 26 of the syringe socket 24 acts to receive the forward portion of this overcap when the syringe body 6 is forced forward against and into the overcap during activation of the syringe. As best understood from FIG. 25, this rearrangement facilitates assembly. The cap 20 is replaced by a driver in the form of a tubular cylindrical element 21, which snaps into the opening of the syringe socket 24 as shown in FIG. 18 in a position in which it covers the rear of the protosyringe, and from which position it can be driven forward to activate the assembly. The element 21 has a bottom aperture to accommodate the plunger 18. The stopper 54 is replaced by a flexible sheath 54 similar to the shield 46, since this is found to simplify assembly and provides complete coverage of the needle 40.

It will be noted that the plunger 18 in the embodiment of FIGS. 17 and 18 is provided with ribs 18 at its distal end. This facilitates an alternative mode of activation of the assembly in which the plunger 18 is assembled to the piston 14 prior to activation, and activation is achieved by pressure on the plunger. This initially drives the hub forward so that the cannula 40 penetrates the closure of he vial 2, then drives the cap 12 into the overcap 35 to penetrate the closure of the protosyringe so that the contents of the latter may be delivered into the vial. The ribs 18a abut the periphery of the opening in the bottom of the driver 21 as the plunger nears the end of its stroke, and presses forward the driver so that it snaps into the sleeve 24, thus signalling the completion of activation.

Various modifications are possible within the scope of the invention, the above description being of a presently preferred example. For instance, the needle 40 could be permanently secured to the hub 34, and the pawls in the vial omitted. Such an arrangement does not provide the user with any choice as to the needle to be used on the finished syringe, and needle length may be severely limited by the need to avoid excess needle extent to the vial 2, which would make it difficult to aspirate its contents.

Likewise, the bottomless vial 4 may be replaced by other forms of protosyringe such as cartridges, or by a prefilled syringe provided with an elastomeric closure covering a luer connection, the front end of the syringe accepting an overcap providing such a needle connection and acting to retain the hub. Such an arrangement is exemplified in FIG. 10, which shows the bottomless vial replaced by a protosyringe which is a conventional prefilled syringe having a conventional luer nozzle 101 protected by a protective rubber sealing cap 100 over a front end of the syringe body, and the syringe socket 24 is modified in shape to receive the body 6 of the syringe, with longitudinal internal ribs 102 to grip the syringe body. As before, a cap 20 prevents the syringe body from being driven fully into the syringe socket 24 until activation is required, and the end 50 of the shield 46 rests against the cap 100 to help maintain sterility of the zones to be penetrated by the needle 44.

Yet further forms of protosyringe may be employed. For example, a known form of diluent vial comprises a body 6 in the form of a glass tube with a piston at both ends. The piston at one end is similar to the piston 14 with an extension similar to the extension 16. The piston at the other end fulfils the function of the neck 8, stopper 10 and cap 12 of the bottomless vial shown in FIG. 1. In conventional use, this other end of the vial is inserted into an open end of a sleeve which at its other end supports a luer or needle externally and an axial hollow pin projecting internally. The piston at the other end of the vial has an axial passage, through the piston and an outward extension of the piston, closed at its outer end by a bung which is displaced by the hollow pin on insertion of the vial into the sleeve, thus establishing communication between the needle or luer and the interior of the vial. Protosyringe from a vial into a syringe is completed by applying a plunger to the piston at the first end. This type of protosyringe can be substituted in the present invention for that shown in FIG. 1 or FIG. 17. During activation, the overcap 16 or 35 will be driven into the extension of the piston at said other end of the vial so that the needle 44 penetrates the sheath 46 and displaces the bung. The bung may be replaced by an integral septum in the passage of the piston which is penetrated by the needle 44.

The syringe socket itself may be made detachable from the completed syringe except for the overcap, or may be truncated in length as shown in FIGS. 11 and 12. It will be seen that the syringe socket 24 is shortened and reduced in diameter to receive the cap 12 of a bottomless vial, the syringe socket being pushed down over the cap 12 to engage the shoulder of the syringe body 6.

On activation of the syringe the hub 34 is driven downwardly relative to the end portion 26 of the socket 24 from the position shown in FIG. 11 to the position shown in FIG. 12. In the position shown in FIG. 11, the end 50 of the rubber shield 46 rests against the closure 10 so as to provide a protected contact zone, which is penetrated by the needle 44 on the hub 34 as the hub is driven downwardly through the guide 52 until a flange 35 on the bottom of the hub 34 contacts the closure 10. At this point the needle 44 establishes communication with the interior of the body 6 of the protosyringe.

Figure 22:
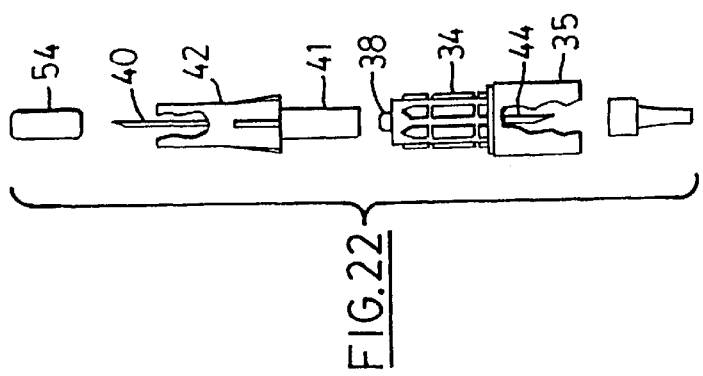
FIG. 22 is an exploded view of components of a hub assembly used in the embodiment of FIG. 21.
Figure 21:
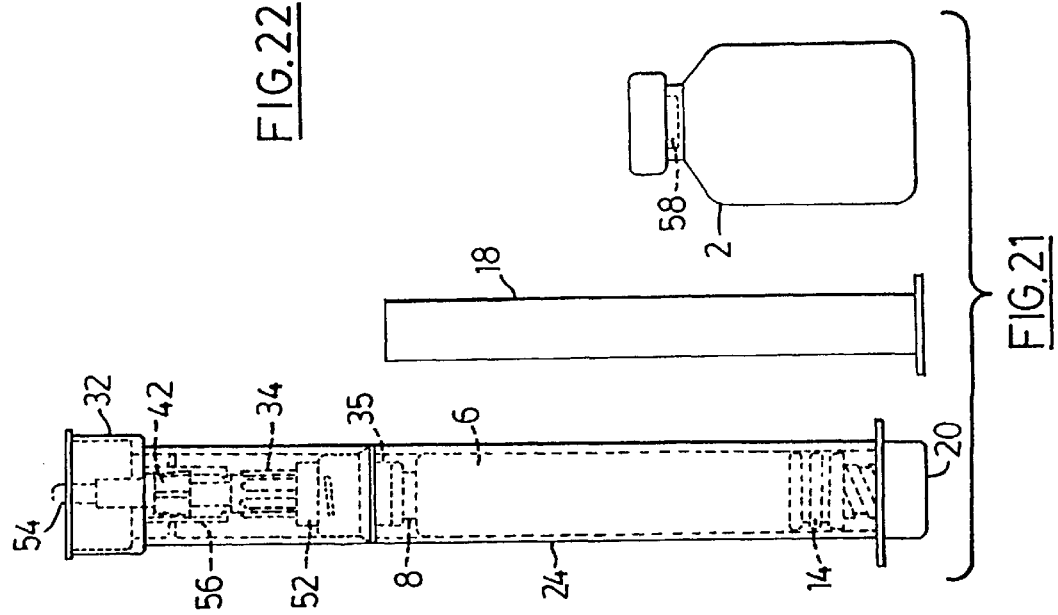
FIG. 21 illustrates the assembled components of a further embodiment of assembly according to the invention.

FIG. 21 shows how the arrangement of FIGS. 11 and 12 (or FIGS. 19 and 20 considered below) may be used in an arrangement in which the assembly is activated by insertion of the vial 2. As best seen in FIG. 22, the component 42 is lengthened and modified so that it, the penetrable shield 54 on the cannula 40, and the cannula 40 itself, project into the vial socket 32. On insertion of the vial 2, the shield 54 is pressed into a recess in the arrangement 42 so that it is penetrated by the cannula, which also penetrates the closure of the vial 2, and the vial closure presses on the component 42 so as to drive the cannula 44 through its sheath or shield and the penetrable closure of the protosyringe. If the modification of FIGS. 19 and 20 is used, with a hub 34 modified as shown in FIG. 22 so that the flange 35 provides the overcap, this driving action also drives the overcap 35 onto the cap of the protosyringe. If the arrangement of FIGS. 11 and 12 is used, the cap of the protosyringe is already lodged in the overcap.

FIG. 13 illustrates an alternative means of driving the hub 34. The luer spigot 38 of the hub 34 is covered by a conventional moulded cover 104, shown in section in FIG. 13, screwed into the socket 36 and providing a convenient driver for the hub which can be unscrewed and discarded preparatory to fitting a needle to the luer of the hub.

FIGS. 14 and 15 illustrate an alternative driver arrangement, making use of a known type of adapter used to couple syringes to flexible mini-bags so that the contents of the syringe may be discharged into the bag and mixed with the contents of the latter. The adapter 106 consists of a tube 108 which has an internally threaded socket 118 at one end for screwing in the present case on to complementary external threads on the portion 26 of a syringe socket 24, and slots 110 at the other end to engage lugs on a nipple of the bag so that the nipple is guided into the adapter concentrically aligned with a needle 112 fitted to the spigot 38 of the hub 34. A cap 114 covers the slotted end of the tube 108, and has a concentric internal tubular extension 116 that sheathes the needle 112, and extends the socket 36 of the hub 34 when the latter is in the position shown in FIG. 11, with the tube 108 extending only part way into the cap 114. Pushing further on the cap will force the hub 34 from the position shown in FIG. 11 to the position shown in FIG. 12, thus activating the syringe. The cap 114 may then be removed, and the syringe applied to a mini-bag as shown in FIG. 16. Alternatively the tube 10 may also be removed providing a ready to use syringe.

Instead of a protosyringe in the form of a bottomless vial, the arrangement of FIGS. 11, 12, 14 and 15 may also be used to activate a regular pharmaceutical vial so that its contents may be mixed with those of a mini-bag or other flexible bag. Liquid from the flexible bag may be caused to enter the activated vial through the needle, and the admixed contents of the vial then allowed to run back into the bag through the needle by suitable manipulation of the bag and the attached activated vial.

The arrangement shown in FIGS. 11 and 12 may also be modified as shown in FIGS. 19 and 20 by extending the flange 35 of the hub 34 to form the overcap (see also FIG. 22). In order to accommodate downward movement of the overcap while preventing inward movement of the protosyringe, the reduced diameter portion of the syringe socket is extended downward as at 27 to form a shoulder limiting insertion of the protosyringe.

Figure 23:
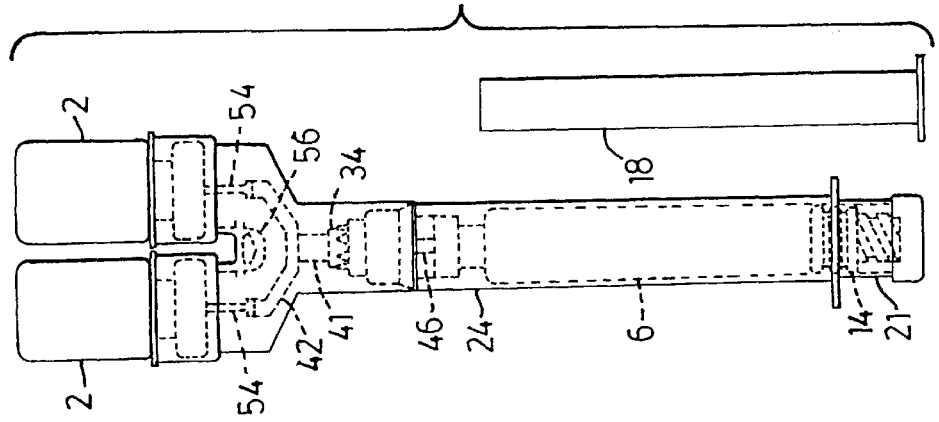
FIG. 23 illustrates a modification of the embodiment of FIG. 18, showing how the assembly of the invention may be used to activate pharmaceuticals having more than two components.

FIG. 23 shows a modification of the embodiment of FIGS. 17 and 18 to allow preparation of a three component pharmaceutical. The vial socket 22 is bifurcated, as is the component 42, so as to provide two vial sockets 30, and two needles which are not seen since they are covered by sheaths 54. On activation of the assembly by driving the driver 21 into the syringe socket 24, the closures of the vials will be penetrated simultaneously, enabling liquid from the protosyringe body 6 to enter both vials 2 and dissolve or suspend their contents. On activation, latch members 56 engage the component 42 to retain it, as in previous embodiments.

A further vial socket 30 and a further branch of the component 42 may be provided for each additional component to be handled.

Figure 24:
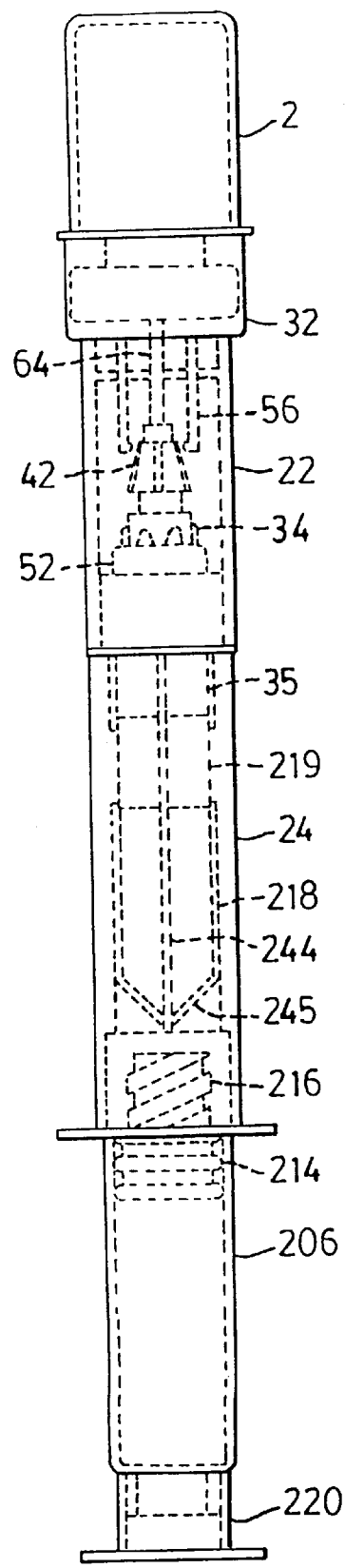
FIG. 24 illustrates an assembly in accordance with a further embodiment of the invention.

Referring now to FIG. 24, the principles of the invention may also be utilized with protosyringes in the form of a shell vial (or as shown, the functional equivalent of a shell vial produced by reversing a bottomless vial 206 as described in U.S. Pat. No. 5,364,369A and applying a driver cap 220 to its cap end). Such shell vials are normally formed into a completed syringe by screwing a threaded extension 216 of a piston 214 into a free end of a plunger stem within a concentric syringe shell connected to the other end of the plunger. A double ended needle extends axially of the plunger stem and out of its other end. Screwing the extension 216 fully onto the plunger stem causes the needle to penetrate the piston so that the contents of the shell vial may be expelled through the needle by driving the vial onto the plunger stem. Such an arrangement is described in U.S. Pat. No. 5,171,214A already referenced above. In the present instance, a syringe socket 224 provides the shell, and the hub assembly utilized in the embodiment of FIGS. 1–10, modified as shown in FIGS. 17 and 18, is further modified by providing an elongated cannula 244 surrounded by a concentric plunger stem 218 positioned on the cannula by passing through a flange 245 and entering the overcap 35. The length of the cannula 244 is such that it ends short of a penetrable septum (not shown) within the piston 21 with the components in the unactivated state shown in FIG. 24, with the piston extension 216 screwed into a threaded socket at the bottom of stem 218.

The assembly is activated by driving the shell vial upwardly so that a reduced diameter portion 219 of the stem 228 enters the overcap 35, permitting the cannula 244 to perforate the septum in the piston. Further upward movement causes the cannula supported at the upper end of the hub to penetrate the sheath 64 and the penetrable closure of the vial 2, whereafter activation can proceed as previously described save that the shell vial 206 is manipulated in place of a conventional plunger.

Figure 25:
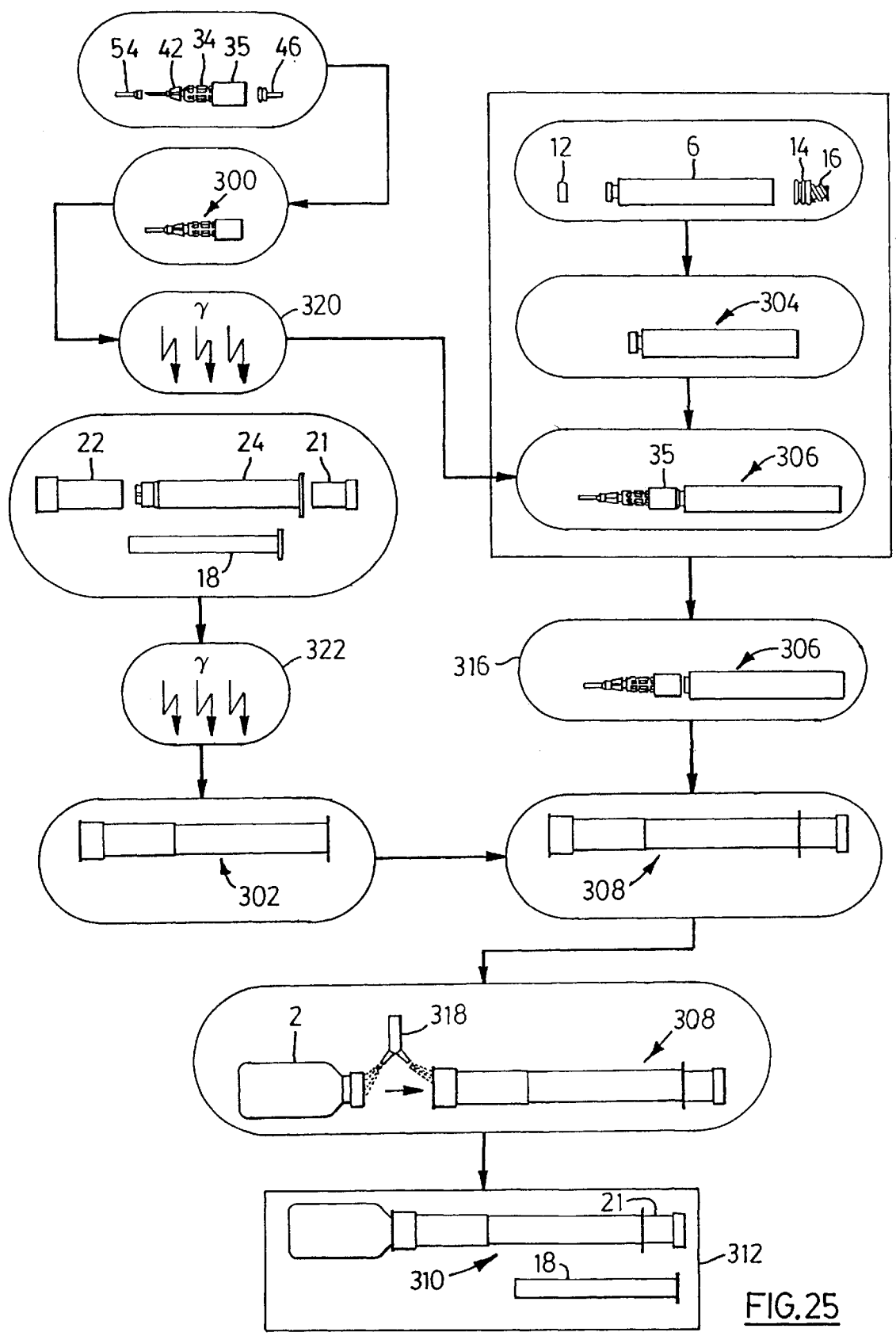
FIG. 25 is a flow diagram illustrating the preparation of assemblies in accordance with the embodiment of FIGS. 17 and 18.

Referring now to FIG. 25, there is shown a flow diagram of the preparation of an assembly in accordance with the invention, specifically the embodiment of FIGS. 17 and 18.

Starting at the top left, the parts 34, 35, 42, 46 and 64 are assembled to form the hub assembly 300, which is then sterilized by gamma radiation (step 320). Within a clean room 314 (top right) the parts 6, 12, 14, 16 are assembled and filled to provide a protosyringe 304 to the cap of which the overcap 35 is applied, but not far enough for the cannula within the overcap 35 to penetrate the shield or sheath 46, to provide subassembly 306, which then passes through an inspection station 316.

In the meanwhile parts 21, 22 and 24 are assembled to provide a subassembly 302 and, together with the plunger 18, sterilized by gamma radiation at 322. The assembly 306 of protosyringe and hub assembly is inserted into the assembly 302 under a laminar flow hood to provide the assembly 308, whereafter, in the same environment, a vial 2, from which any protective metal disc on the cap has been flipped off, is inserted into the vial socket of the assembly 308, which corresponds exactly to that of FIG. 18. The contacting surface of the penetrable closure 58 (see FIG. 1) of the vial 2 and the surface 50 of the shield 64 are sterilized by a high intensity ultraviolet flash or an antiseptic spray 318 during this step, whereafter the resulting assembly 310 together with the plunger 18 is sealed into a plastic tray 312. The tray is vacuum formed with a recess shaped to correspond to the profile of the assembly 310. In particular, it is advantageous that this recess snugly embraces the narrower portion of the actuator 21 to avoid any possibility of inadvertent activation prior to use occasioned by shock or rough handling.

Variations are of course possible in this procedure. For example, the protosyringe 304 like the vial might be pre-produced and terminally sterilized, and assembled to the hub assembly to produce the assembly 306 in a similar manner to combination of assemblies 302 and 308.

In the embodiments described above, activation of the protosyringe involves penetration of the closure of the protosyringe by a second cannula on the hub, but the invention is also applicable to protosyringes activated by other means. In U.S. Pat. No. 3,967,759 (Baldwin), there is disclosed a protosyringe in which the closure at the capped end of the body of the protosyringe is a plug lodged in an end of a tubular body, which closure is breached by ejection of the plug into a hollow interior of the cap such that the contents of the syringe may bypass the plug within the cap.

Such a protosryinge is activated by application of fluid pressure to the plug by the application in turn of longitudinal pressure to the piston of the protosyringe by a plunger, and thus the second cannula and its associated sheath is not required.

This arrangement is exemplified in FIGS. 26 and 27, in which the same reference numerals are used to identify the same parts as in FIGS. 1–8 or 17, and only the points of difference will be discussed in detail. The components shown in the left hand portions of FIG. 26, with the exception of a filter 400, are essentially identical to the corresponding components of the embodiment of FIGS. 17 and 18, but the protosyringe shown in the right hand of FIG. 26 is essentially similar to that described with reference to FIGS. 1–4 of U.S. Pat. No. 3,967,759 (Baldwin), the text and drawings of which are incorporated herein by reference, except that the piston retainer 402 pressed into the rear of the body 6 is formed without the external flange 25 shown in the Baldwin patent, and the connector 37 of the Baldwin patent is replaced by a more conventional luer connector 36, 38 forming a hub integral with the cap 12, which otherwise corresponds to the cap 31 of the Baldwin patent, and is secured to the body 6 by means of a flange 404 pressed onto the body. The plug 10 corresponds to the plug 51 of the Baldwin patent, and may be formed with ribs similar to the ribs 53 of Baldwin or other means to ensure that, once the plug moves forward from the body 6 into the cap 12, the seal formed by the plug remains broached, and liquid can bypass the plug. There are other systems known using displaceable plugs generally similar to that disclosed in the Baldwin patent but differing in detail in the means used to ensure that the plug remains bypassed once broached, and these could also be utilized.

An adaptor 400 containing a filter may be provided secured to the connector 41 on the cannula 40, the adaptor being a press fit on the luer 38, such that when the cannula 40 is captured by the detents 56 and the portion 22 is removed, the adaptor 400 discarded with the cannula 40 and the portion 22. This enables a filter, incorporated in the adaptor 400, to be utilized during transfer of liquid between the vial 2 and the protosyringe during an activation process, so that any particulate may be removed from the reconstituted pharmaceutical as it is drawn back into the protosyringe.

The activation process is generally quite similar to that previously described. Referring to FIG. 27, pressing down on the activation cap 21 causes the latter to move into the open end of the socket 24 and press the piston retainer 402 at the rear end of the body 6 so as to move the cap 12 into the overcap 26. This moves the hub assembly formed by the luer 34, adaptor 400 and cannula 40 upwardly within the sleeve 22 until the cannula 40 pierces the closure of the vial 2. The plunger 18 can then be attached to the piston 14, and on applying pressure to the plunger, the plug 10 is moved forward to broach the closure of the protosyringe at its capped end, allowing the contents of the syringe to be discharged through the cannula 40 into the vial 2. After admixture (See FIGS. 4–9), the dissolved pharmaceutical is withdrawn back into the protosyringe through the cannula 40 and the filter in adaptor 400, and the filled syringe is removed as shown in FIG. 9, leaning behind the cannula 40 and the adaptor 400 containing the filter, and presenting the luer 34 for attachment of a hypodermic needle or other injection instrumentality.

In another possible variation, the portion of cap 12 beyond the body 6 has a smaller rather than larger internal diameter than the body 6, and the plug 10 is initially lodged in that portion of the cap 12. The 44 of the FIG. 1 or 17 embodiment is replaced by an activator rod, and the hub is made axially movable relative to the protosyringe as in the previous embodiments, so that on actuation of the syringe, the rod is projected against the plug 10 in the cap 12 and dislodges it into the body 6 to broach the seal of the protosyringe.

What is claimed is:

1. An activation assembly for preparing a prefilled syringe from separately prepackaged components of a multicomponent pharmaceutical preparation, the assembly comprising a two part tubular body; the body defining in a first part a first cylindrical recess at one end with a diameter to receive, as a sliding fit, a discharge end of a cylindrical body of a protosyringe at which end is located a closure, broachable on activation of the protosyringe, the recess also receiving a substantial portion of the cylindrical body of the protosyringe, which contains a first liquid component of the pharmaceutical preparation and which is provided at its opposite end with a piston displaceable longitudinally of the cylindrical body and forming a hermetic seal therewith; a second cylindrical recess defined in an opposite end of the tubular body by a second detachable part to receive a cap securing a penetrable closure at the neck of a pharmaceutical vial containing a second component of the pharmaceutical preparation; the tubular body defining in said first part a passage connecting the cylindrical recesses; a hub movable longitudinally of the tubular body within the passage; a transfer cannula extending longitudinally of the tubular body from said hub to a distal end directed towards the second recess; a penetrable shield member covering the distal end of the cannula and located to contact a penetrable closure of a pharmaceutical vial inserted in the second cylindrical recess and a hollow cylindrical overcap concentric with the hub and located within the tubular body in the first cylindrical recess, the overcap being connected to the hub to limit movement of the latter into the passage; the depth of the cylindrical recesses, the length of the passage connecting the recesses, the extent of the transfer cannula from the hub, and the location of the overcap in the first cylindrical recess being such that upon a protosyringe received in the first cylindrical recess and a vial received in the second recess being displaced towards each other, the overcap is displaced onto the discharge end of the protosyringe and the hub moves longitudinally so that the transfer cannula penetrates the penetrable shield member and the penetrable closure of the vial to place the protosyringe and the vial in fluid communication through the transfer cannula;

wherein the protosyringe and the vial can be driven directly towards each other to effect penetration of the shield member and the penetrable closure of the vial, wherein a portion of the hub supporting the transfer cannula is separately formed and detachable from the hub, the hub having a luer on which said separately formed portion is releasably lodged, and wherein means is provided within the detachable part of the tubular body to detain, within the tubular body, said portion of the hub and the transfer cannula when the cannula is driven into a position penetrating the cap of the pharmaceutical vial.

2. An assembly according to claim 1, wherein the closure of the protosyringe is a penetrable closure and the hub has a further cannula directed towards the first recess and with a penetrable shield member covering its distal end, the further cannula being of a length such as to penetrate its shield member and the closure of the protosyringe when the protosyringe and the vial are driven towards each other.

3. An assembly according to claim 1, wherein the overcap is integral with said first part of the tubular body.

4. An assembly according to claim 1, wherein said overcap is integral with the hub.

5. An assembly according to claim 2, wherein a shoulder is defined in the first recess limiting movement of the cylindrical body of a protosyringe into the first recess such that it limits its engagement with the overcap to a point where it contacts the shield member associated with the cannula directed towards the first recess without causing penetration of the shield member or the penetrable closure of the protosyringe, and a cap of a vial can be linearly driven far enough into the second recess for the transfer cannula directed towards the second recess to penetrate its associated shield member and the penetrable closure of the vial, and for the penetrated vial to drive the hub downwards to force the overcap onto the cap of a protosyringe fully inserted in the first recess, and to drive the cannula directed towards the first recess through both the shield member associated therewith and the penetrable closure of the protosyringe.

6. An assembly according to claim 2, wherein a shoulder is defined in the second recess limiting movement of a cap of a vial into the second recess to a location contacting the shield member associated with the transfer cannula directed towards the second recess without causing penetration of the shield member or a penetrable closure of the vial, and a cap of the protosyringe can be linearly driven far enough into the first recess for the cap to enter the overcap far enough that the further cannula directed towards the first recess penetrates both the shield member associated with further cannula and the penetrable closure of the protosyringe and drives the hub sufficiently towards the second recess that the transfer cannula directed towards the second recess penetrates both the shield sealing member associated therewith and a penetrable closure of a vial fully inserted in the second recess.

7. An assembly according to claim 5, wherein part of the tubular body defining the second recess includes a detent limiting insertion of a cap of a vial, to a point at which a penetrable closure of the vial contacts the shield member associated with the transfer cannula directed towards the second recess without resulting in penetration of the shield member or penetrable closure, until sufficient pressure is applied to the vial to overcome the detent.

8. An assembly according to claim 5, wherein the overcap includes a detent limiting insertion of a cap of a protosyringe to a point at which a penetrable closure of the protosyringe contacts the shield member associated with the further cannula directed towards the first recess without resulting in penetration of the shield member or penetrable closure, until sufficient pressure is applied to the protosyringe to overcome the detent.

9. An assembly according to claim 6, wherein the overcap includes a detent limiting insertion of a cap of the protosyringe, to a point at which the penetrable closure of the protosyringe contacts the shield member associated with the further cannula directed towards the first recess without resulting in penetration of the shield member or penetrable closure, until sufficient pressure is applied to the protosyringe to overcome the detent.

10. An assembly according to claim 2, wherein the shield member is of elastomeric material and disposed within the assembly so that area of this members will enter resilient contact with the areas of the penetrable closures of the protosyringe and the vial which are concentric with the cannulas when the protosyringe and the vial are installed in their respective cylindrical recesses.

11. An assembly according to claim 1, wherein the body defines, in said second part, plural second cylindrical recesses to receive caps of plural pharmaceutical vials and said hub comprises plural cannulas extending towards said second cylindrical recesses, and plural sealing members associated with said plural cannulas.

12. An assembly according to claim 2, wherein the protosyringe is a shell vial closed by a piston having a penetrable septum and capped by a member telescopically engageable with the overcap to permit the further cannula directed towards the first recess to penetrate the septum.

13. An assembly according to claim 1, wherein a tubular cylindrical element is lodged in an entrance to the first recess to retain the protosyringe therein, the cylindrical element being driven further into the recess during activation of the assembly.

14. An assembly according to claim 1, further including a protosyringe and a pharmaceutical vial.

15. An assembly according to claim 2, further including a protosyringe and a pharmaceutical vial.

16. An assembly according to claim 1, wherein the separately formed portion of the hub includes an in-line filter.

17. An assembly according to claim 1, wherein the broachable closure of the protosyringe is a longitudinally displaceable plug.

18. An assembly according to claim 17, wherein the plug is displaceable from the body of the protosyringe into an end cap by fluid pressure developed within the body of the protosyringe by means of a plunger applied to its piston.

19. A method for producing the assembly of claim 14 including two components of a pharmaceutical, at least one of which is liquid, which can be activated to provide a prefilled syringe, characterized in that it comprises the steps of producing a sterile protosyringe containing a liquid component of the pharmaceutical, and a sterile pharmaceutical vial containing a second component of the assembly, producing a subassembly comprising said first and second sockets and a guide, producing a hub assembly, sterilizing said subassembly and said hub assembly, and inserting said hub assembly and said protosyringe into said first socket and said vial into said second socket while maintaining sterility at the zones of contact of the shields with the penetrable septums.

20. A method for producing the assembly of claim 15, including two components of a pharmaceutical, at least one of which is liquid, which can be activated to provide a prefilled syringe, characterized in that it comprises the steps of producing a sterile protosyringe containing a liquid component of the pharmaceutical, and a sterile pharmaceutical vial containing a second component of the assembly, producing a subassembly comprising said first and second sockets and a guide, producing a hub assembly, sterilizing said subassembly and said hub assembly, and inserting said hub assembly and said protosyringe into said first socket and said vial into said second socket while maintaining sterility at the zones of contact of the shields with the penetrable septums.

21. In an assembly for preparing a pre-filled syringe from separately prepackaged components of a multi-component pharmaceutical preparation, comprising:

a pharmaceutical vial having a penetrable seal and containing a first component of a pharmaceutical preparation, a syringe-forming component having a broachable seal and defining a vessel containing a second liquid component of the pharmaceutical preparation, and a tubular transfer device having sockets at opposite ends for receiving respectively at least a portion of the vial including said seal of the vial and at least a portion of said syringe-forming component including said seal of the syringe-forming component, the transfer device containing a transfer needle extending towards the end of the transfer device for receiving the vial, and broaching means extending towards the end of the transfer device for receiving the syringe-forming component, such as to penetrate said vial seal and broach said syringe-forming component when said vial and said syringe-forming component are driven towards each other within the transfer device and to establish a liquid passage between the vessel of the syringe-forming component and the vial, wherein the structure defining the liquid passage established between the vessel and the vial includes the transfer needle for penetrating the vial coupled to a standard luer, and the syringe-forming component together with a portion of the transfer device comprising said luer is detachable from the remainder of the transfer device including the transfer needle to provide a syringe presenting said luer for reception of injection means.

22. An assembly according to claim 21, wherein the needle and the broaching means of the transfer device are mounted on a hub assembly axially displaceable within the tubular transfer device body defining said sockets, the tubular transfer body being separable into two portions after the syringe-forming component and the vial are driven toward each other such that the needle remains captive within a portion defining the vial socket.

23. An assembly according to claim 22, wherein the tubular transfer device includes an overcap driveable onto a portion of the syringe-forming component which comprises the broachable seal.

* * * * *